(12) United States Patent
Graeber et al.

(10) Patent No.: US 9,448,178 B2
(45) Date of Patent: Sep. 20, 2016

(54) INTEGRATED MICROFLUIDIC RADIOASSAY AND IMAGING PLATFORM FOR SMALL SAMPLE ANALYSIS

(71) Applicant: THE REGENTS OF THE UNIVERSITY OF CALIFORNIA, Oakland, CA (US)

(72) Inventors: Thomas G. Graeber, Pacific Palisades, CA (US); Hsian-Rong Tseng, Los Angeles, CA (US); Arion F. Hadjioannou (Chatziioannou), Los Angeles, CA (US); Cong Fang, Newbury Park, CA (US); Yanju Wang, Los Angeles, CA (US); Nam T. Vu, Redondo Beach, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 176 days.

(21) Appl. No.: 13/783,283

(22) Filed: Mar. 2, 2013

(65) Prior Publication Data

US 2013/0244257 A1 Sep. 19, 2013

Related U.S. Application Data

(63) Continuation of application No. PCT/US2011/051114, filed on Sep. 9, 2011.

(60) Provisional application No. 61/381,332, filed on Sep. 9, 2010.

(51) Int. Cl.
*B01L 3/00* (2006.01)
*G01N 21/75* (2006.01)
(Continued)

(52) U.S. Cl.
CPC ......... *G01N 21/75* (2013.01); *B01L 3/502761* (2013.01); *C12Q 1/485* (2013.01);
(Continued)

(58) Field of Classification Search
None
See application file for complete search history.

(56) References Cited

U.S. PATENT DOCUMENTS

| 6,384,401 B1 | 5/2002 | Jensen |
| 7,105,304 B1 | 9/2006 | Nikiforov et al. |

(Continued)

FOREIGN PATENT DOCUMENTS

| WO | 03001889 A2 | 1/2003 |
| WO | 2007081385 A1 | 7/2007 |

(Continued)

OTHER PUBLICATIONS

Korean Intellectual Property Office, International Search Report and Written Opinion (pp. 1-9) issued on May 1, 2012 for corresponding International Patent Application No. PCT/US2011/051114 with claims searched (pp. 10-17) pp. 1-17.

(Continued)

*Primary Examiner* — Rebecca Martinez
(74) *Attorney, Agent, or Firm* — O'Banion & Ritchey LLP; John P. O'Banion

(57) ABSTRACT

An immunocapture-based in vitro kinase assay on an integrated polydimethylsiloxane (PDMS) microfluidics platform that can reproducibly measure kinase activity from as few as 3,000 cells is described. For this platform, the standard radiometric $^{32}$P-ATP labeled phosphate transfer assay was adopted. Implementation on a microfluidic device required the development of methods for repeated trapping and mixing of solid-phase affinity micro beads. A solid state beta-particle camera imbedded directly below the microfluidic device was used to provide real-time quantitative detection of the signal from this and other microfluidic radio bioassays. The integrated device can measure ABL protein kinase activity from BCR-ABL positive leukemia patient samples, and can measure the small molecule phosphorylation such as phosphorylation of the deoxycytidine analog $^{18}$F-FAC by deoxycytidine kinase (dCK) isolated from cell lysates.

20 Claims, 7 Drawing Sheets

(51) Int. Cl.
    *C12Q 1/48* (2006.01)
    *G01N 33/543* (2006.01)
    *G01N 33/573* (2006.01)

(52) U.S. Cl.
    CPC ...... *G01N33/54366* (2013.01); *G01N 33/573* (2013.01); *B01L 3/502707* (2013.01); *B01L 2200/0668* (2013.01); *B01L 2300/088* (2013.01); *B01L 2300/0816* (2013.01); *B01L 2400/0481* (2013.01); *B01L 2400/0487* (2013.01); *B01L 2400/086* (2013.01)

(56) References Cited

U.S. PATENT DOCUMENTS

| | | | |
|---|---|---|---|
| 2003/0077570 | A1 | 4/2003 | Chiem et al. |
| 2004/0219523 | A1 | 11/2004 | Epstein |
| 2004/0229284 | A1* | 11/2004 | Luciw et al. ............. 435/7.1 |
| 2004/0245102 | A1 | 12/2004 | Gilbert et al. |
| 2005/0142033 | A1 | 6/2005 | Glezer et al. |
| 2007/0075010 | A1* | 4/2007 | Gilbert et al. ............. 210/321.6 |
| 2009/0234202 | A1 | 9/2009 | Goix et al. |

FOREIGN PATENT DOCUMENTS

| | | | |
|---|---|---|---|
| WO | 2007081387 | A1 | 7/2007 |
| WO | WO2007/124085 | * | 11/2007 |
| WO | 2008079320 | A1 | 7/2008 |

OTHER PUBLICATIONS

Jeong Hoon Lee et al., "Microfluidic concentration-enhanced cellular kinase activity assay," Journal of the American Chemical Sociemty, 2009, vol. 131, No. 30, pp. 10340-10341.

Wu, D. et al. "A solid-phase Bcr-Abl kinase assay in 96-well hydrogel plates" Anal Biochem. Apr. 1, 2008; vol. 375(1), pp. 18-26.

Matthew B. Kerby et al. "Selective Ion Extraction for High Throughput Screening with a Microfluidic Enzyme Assay" Journal of Laboratory Automation, Dec. 1, 2002, vol. 7, No. 6, pp. 114-119.

Dunne, J., et al. "Comparison of on-chip and off-chip microfluidic kinase assay formats," Assay and Drug Development Technologies. Apr. 2004, vol. 2(2) pp. 121-129.

Yamamoto, S, et al. "Development of a high resolution beta camera for a direct measurement of positron distribution on brain surface," Nuclear Science, IEEE Transactions, Aug. 1997, vol. 44 pp. 1538-1542.

Blackwell, L.J., et al., "High-Throughput Screening of the Cyclic AMP Dependent Protein Kinase (PKA) Using the Caliper Microfluidic Platform," High Throughput Screening, Methods in Molecular Biology, vol. 565, Jul. 9, 2009, pp. 225-237.

Shah, et al. "Position sensitive APDs for small Animal PET imaging," Nuclear Science, IEEE Transactions, Feb. 2004, vol. 51, Issue: 1, pp. 91-95.

Levin, C., et al., "Investigation of position sensitive avalanche photodiodes for a new high-resolution PET detector design," Nuclear Science, IEEE Transactions, Jun. 2004, vol. 51, Issue: 3, pp. 805-810.

\* cited by examiner

INTEGRATED MICROFLUIDIC RADIOASSAY AND IMAGING PLATFORM FOR SMALL SAMPLE ANALYSIS

CROSS-REFERENCE TO RELATED APPLICATIONS

This application is a 35 U.S.C. §111(a) continuation of PCT international application number PCT/US2011/051114 filed on Sep. 9, 2011, incorporated herein by reference in its entirety, which is a nonprovisional of U.S. provisional patent application Ser. No. 61/381,332 filed on Sep. 9, 2010, incorporated herein by reference in its entirety. Priority is claimed to each of the foregoing applications.

The above-referenced PCT international application was published as PCT International Publication No. WO 2012/034094 on Mar. 15, 2012 and republished on Jun. 21, 2012, and said publications are incorporated herein by reference in their entirety.

STATEMENT REGARDING FEDERALLY SPONSORED RESEARCH OR DEVELOPMENT

This invention was made with Government support under Grant Number EB002101 awarded by the National Institutes of Health. The Government has certain rights in the invention.

INCORPORATION-BY-REFERENCE OF MATERIAL SUBMITTED ON A COMPACT DISC

Not Applicable

BACKGROUND OF THE INVENTION

1. Field of the Invention

This invention pertains generally to microfluidic devices and diagnostic schemes, and more particularly to a microfluidic imaging platform for radioactivity-based biological activity assays on protein or small molecule substrates.

2. Description of Related Art

The observation of abnormal biological activity can be an important diagnostic tool for determining the presence of human diseases as well as a focus for treatment and the study of diseases. Pharmaceuticals directed to promoting or inhibiting certain physiological functions have provided relief of symptoms as well as the successful treatment of many diseases. For example, the 518 known kinases in humans constitute nearly two percent of the human genome and represent one of the largest classes of drug targets pursued by pharmaceutical companies. With as many as 50% of intracellular proteins regulated by phosphorylation-mediated signal transduction, kinases play a major role in numerous aspects of cell biology, including proliferation, differentiation, secretion and apoptosis. Kinase dysfunction has been implicated in a wide variety of diseases including many cancers.

Kinase-related signaling measurements that are taken directly from patient samples often involve detecting the consequences of activity, for example the resulting downstream phosphorylation patterns. Direct measurement of kinase activity from patient samples can greatly complement these phosphoprofiling techniques.

The broad interest in targeting kinases for drug discovery has lead to the development of numerous kinase assay technologies. Among them, radiometric assays represent the earliest kinase assay technology and are generally considered the "gold standard" for determining basic enzyme properties. These assays utilize ATP radiolabeled on the γ-phosphate (generally $^{32}P$ or $^{33}P$). In a kinase reaction, the radioisotope is transferred from ATP to the acceptor molecule, and the rate of product formation can be quantified by measuring the extent of isotope incorporation. Radiometric kinase assays are useful for determining basic enzyme properties, in part, because radiolabeling of reaction substrates does not alter their intrinsic biochemical and physical properties.

Although they are adopted as the primary technology for kinase profiling services, all radiometric assays suffer from the same drawback in that they are difficult to miniaturize. The requirement of a sufficient number of input cells makes it difficult to study kinase activity on small volume samples. For example, BCR-ABL is a constitutively activated, oncogenic tyrosine kinase that causes both chronic myeloid leukemia (CML) and B-cell acute lymphoblastic leukemia (B-ALL). BCR-ABL inhibitors, such as imatinib (Gleevec) are widely used in clinical applications but patients often acquire drug resistance at some point during the treatment. One type of drug resistance is caused by the natural or developed insensitivity of leukemic stem cells to kinase inhibitors. The urgent need for studying kinase activity in patient cancer samples and in cancer stem cells cannot be fully met by conventional radiometric assays due to the limited amount of sample that is available. Thus far, little has been done to miniaturize the in vitro kinase radioassay beyond the 96 well format to make it compatible with limited sample size.

In addition, many fluorescence/luminescence-based assays have emerged to avoid exposure to radioactivity. However, fluorescence assays have their own set of drawbacks including the requirement of a fair amount of cell input, being less quantitative than radiometric kinase assays, and often requiring engineered substrates to be created for each particular kinase. Therefore, the conventional kinase assay is inadequate for evaluation and imaging of small sample sizes.

Accordingly, there is a need for an assay apparatus and method that can provide a reliable, highly sensitive analysis and assay a variety of different kinase or other biological activity without the need for a large sample size. The present invention satisfies this need as well as others and is an improvement over the art.

BRIEF SUMMARY OF THE INVENTION

The present invention is directed to an apparatus and methods for microfluidic, radioactivity-based imaging that does not require large numbers of cells for analysis. The invention is suitable for a broad range of applications that benefit from integrated microfluidic/beta camera imaging detection platforms such as radioactivity-based bioassays, various enzymatic activity assays, various kinase assays, and particularly protein kinase assays (by capturing specific kinases or measuring all of the kinases in a cell) or small molecule kinase assays (such as sugars, nucleosides, and their analogs, e.g. hexokinase/glucose, thymidine kinase, deoxycytidine kinase).

The apparatus preferably provides microfluidic solid-phase reaction control with microfluidic-based sieve valves, circulation chamber, solid phase beads, and a bead capture, release, mix, recapture protocol for solid phase reactions, such as solid-phase-based bioassasys or solid-phase-based radio assays. Microfluidic on-chip capture or immunocapture of small molecules, peptides, kinases, enzymes or other proteins unlabeled or labeled (e.g. with biotin) for subsequent use in bioassasys, via solid phase beads is also provided.

The preferred embodiment of the invention is illustrated with a kinase radioassay of a very small cell sample size. Normally, the input amounts required for a radiokinase assays makes it difficult to study kinase activity on samples with a small number of cells. So far, little has been done to miniaturize the conventional in vitro kinase radioassay beyond the 96 well format to make it capable of dealing with limited sample size. Some other disadvantages of conventional large scale radiometric assays is that they are labor-intensive, have a high cost and are a potential hazard to people handling radioactive materials. Furthermore, regulations controlling the levels of radioisotope that can be used limits the number of plates that can be screened each day, and can limit the desired pace of work. These disadvantages can be avoided with the small scale apparatus of the invention.

In order to assess kinase activity in minute patient samples, an immunocapture-based in vitro kinase assay on an integrated polydimethylsiloxane (PDMS) microfluidics platform was designed that can reproducibly measure kinase activity from as few as 3,000 cells. For this platform example, a standard radiometric $^{32}$P-ATP labeled phosphate transfer assay was selected. Implementation on a microfluidic device required the development of methods for repeated trapping and mixing of solid-phase affinity micro beads. A solid state beta-particle camera imbedded directly below the microfluidic device produces a real-time quantitative detection of the signal from this and other microfluidic radio bioassays. The resulting integrated device can measure ABL kinase activity from BCR-ABL positive leukemia patient samples. The low sample input requirement of the device creates a new potential for direct kinase activity experimentation and diagnostics on a variety of samples including but not limited to patient blood, bone marrow, and needle biopsy samples on normal and tumor tissue.

The apparatus preferably uses a Poly(dimethylsiloxane) (PDMS)-based integrated microfluidic chip architecture of fluidic channels that allows for the execution and automation of sequential physical, chemical and biological processes on the same device with the digital control of operations. The elasticity of PDMS materials enables the parallel fabrication of the micron-scale functioning modules, such as valves, pumps and columns that are necessary for sequential operations.

In addition, fabrication of intricate devices using this technology requires only relatively simple facilities and the fluidic and control networks can be mapped using standard CAD software and transferred onto transparent photomasks. Photolithographic techniques are used to produce a reusable mold onto which a PDMS resin is poured and cured by baking. Access to the fluidic channels is achieved by punching holes through the bulk material, and the devices are readily bonded to glass or silicon substrates. Large arrays of active components, such as valves and pumps, can be created by stacking multiple, individually fabricated layers. When pressurized with air or inert gases, a channel on the control layer that crosses a channel on the flow layer is deflected, sealing the flow channel and stopping fluid movement. This method of valve operation also constitutes the binary switches (e.g., open or closed) of the microfluidics chip.

As illustrated in FIG. 2 and FIG. 3, the preferred chip design contains two isolated and symmetric fluidic modules for individual kinase reactions run in parallel. The fluidic layer channels of both modules are simultaneously controlled by the pressure actuations of their shared bottom control layer. Each module has both i) an upper circulation chamber and bead-trapping column for the immunocapture and kinase reaction steps and ii) a lower bead-trapping column for the final substrate capture step. The upper circulation chamber is designed for manipulating the immunocapture beads through multiple trap and release steps.

A Position Sensitive Avalanche Photodiode (PSAPD)-Based Solid State Beta Camera is incorporated below the chip. Silicon avalanche photodiodes (Pads) can be used for direct X-ray and charged particle detection as well as for scintillation detection. The device has low noise, and high quantum efficiency. The use of compact position sensitive avalanche photodiodes (PSAPD) offers a method of not only charged particle detection but also spatial imaging capability that was not previously available. Coupled together with a microfluidic device, this platform allows for imaging and quantification of low amounts of radioactivity in biological samples on a microfluidic platform.

In one embodiment, the invention is implemented as a single integrated unit, including the microfluidic components, beta camera and custom electronics, that would be controlled, including data output, via a USB connection by a personal computer. The device performs an automated multi-step kinase reaction assay with coupled readout in a single unit, complete from sample loading to final quantitative data.

There are significant benefits of miniaturizing the radiometric kinase assay from macro-scale to micro-scale. First, there is a reduction of the amount of cell input by approximately 1,000 times compared to conventional assays. Thus, this technology allows for direct experimentation on clinical samples that are either precious or perishable. Second, the amount of radioactivity used is decreased by at least one order of magnitude and thus reduce radioisotope handling and disposal, hence reducing radiation safety concerns. Third, the PDMS chips are low in cost to custom design and produce, and their development/prototyping cycles are relatively short. Therefore, combined with reduced need for reagents and sample, the on-chip assay is much less expensive than conventional radiometric assays. In addition, it provides a well controlled microfluidic environment to perform kinase assays more efficiently and faster. Most of the steps in the assay are under digital control, which reduces the cost of labor.

This technology can be applied to monitor kinase activity in precious samples such as biopsies or aspirate in experimental pre-clinical and clinical trials. It is contemplated that the apparatus will become a complementary diagnosis kit for cancer and other disease patients along with already existing assays. This technology and the demonstrated applications in low cell number leukemic systems shows promise for studying signaling pathways in stem cells and/or patient samples in cancer and other disease biologies.

According to one aspect of the invention, a microfluidic chip design is provided that contains valves, sieve valves, and circulation chambers and protocols that can confine solid phase beads and carry out solid phase-based reactions that includes a solid state beta camera, which is typically more quantitative than a fluorescent assay.

According to another aspect of the invention a microfluidic chip is provided that measures the amount of enzymatic reaction product relative to substrate by measuring the incorporation of radioactivity in the protein kinase assay, rather than by electrokinetic separation, electrophoretic separation or mobility shift-based separation as required by conventional large scale assays.

In another aspect of the invention, a chip is provided that can perform a full kinase assay and radioactivity-based readout on-chip without the need for secondary ion mass spectrometric analysis.

In a further aspect of the invention, a chip design is provided that contains valves, sieve valves and circulation chambers that can confine beads and carry out solid phase reactions and these components are used instead of chemical caging to separate and mix various components as required by conventional assays.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 is a schematic diagram of one embodiment of a microfluidic chip with a solid state radiation detector apparatus according to the invention.

FIG. 2a-d are schematic diagrams of the microfluidic immunocapture-based in vitro kinase radio assay (µ-ivkra).

FIG. 3a-d are schematic diagrams of key steps of the operation of the on-chip kinase radio assay shown in FIG. 2a-d.

FIG. 4a-d depict the development of an on-chip in vitro BCR-ABL kinase radio assay.

FIG. 5a-d depict on-chip in vitro BCR-ABL kinase radio assays in leukemic systems.

DETAILED DESCRIPTION OF THE INVENTION

Referring more specifically to the drawings, for illustrative purposes the present invention is embodied in apparatus and methods generally illustrated in FIG. 1 through FIG. 7. It will be appreciated that the apparatus embodiments may vary as to configuration and as to the details of the parts, and that the methods may vary as to the specific steps and sequence, without departing from the basic concepts as disclosed herein. The present invention relates to devices and methods for micro-scale radio assays that enable analysis of small sample sizes in a closed and controlled environment.

Figure 1:
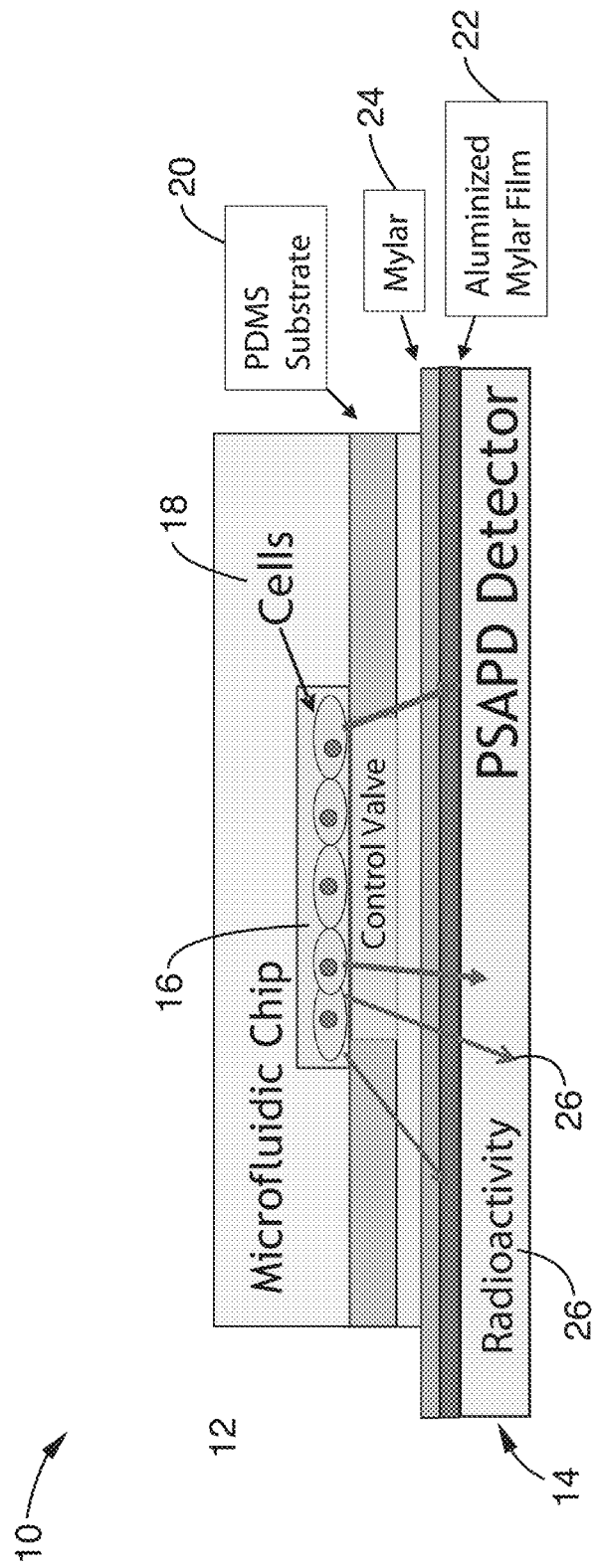

The apparatus and methods of the present invention can be adapted to assay many different biological activities, but a kinase radio assay and microfluidic chip and detector are used to illustrate a preferred embodiment. Turning now to FIG. 1, a schematic diagram of a cross section of one embodiment 10 of a microfluidic chip 12 and the PSAPD detector 14 is shown. In the center of the chip is a microfluidic channel 16 where radioactive cells 18 and solutions can be loaded. Beneath the channel are a series of substrate layers 20 that can be used to control the flow of solutions. The PSAPD detector 14 is sealed from visible light with an aluminized Mylar film 22 and protected by another sacrificial Mylar film 24. Radiation 26 emitted from the microchip is detected and quantified by the PSAPD detector 14.

By coupling a microfluidic platform 12 to a solid-state beta emission detection camera 14, an integrated platform 10 for immunocapture-based in vitro kinase radio assays on minute cancer samples is illustrated. The device executes an automated, multi-step solid-phase binding and enzymatic reaction and provides imaging-based final quantitative readout of the assay. The apparatus and method includes techniques for efficient handling of solid-phase micro-beads that allow for the multiple bind, wash, and solvent exchange cycles required by many affinity-based bioassays. In particular, it was found that bead trapping, release, and homogenization using sieve valves and peristaltic pumps is an efficient and reproducible approach.

The integration of the solid-state beta camera 14 directly underneath the microfluidic platform 12 allows imaging the radioisotope distribution both as a final readout and for real-time monitoring of the operational steps of the assay. The PSAPD-based imaging camera 14 has high sensitivity and very low inherent background (1.5 counts/hour/mm$^2$), making feasible the acquisition of very weak signals over time periods longer than the 20 minutes used here. The imaging camera 14 is preferably coupled with or immediately adjacent to the microfluidic chip 12.

Many bioassays are radioisotope-based and therefore this sensitive imaging device facilitates the miniaturization of these different assays to a microfluidic platform. The stand-alone benchtop embodiment of the device can measure kinase activity from as few as 3,000 cells and opens new possibilities for experimentation directly on minute patient samples from blood draws, bone marrow aspirates and needle biopsies.

In one embodiment, screening of enzyme and putative enzyme inhibitor combinations is provided. In this configuration, the captured enzyme molecules react with a radioactively labeled substrate in the presence of the kinase inhibitor to produce a reaction product, if any. In addition, kinases that have mutations that result in kinase inhibitor insensitivity and thus cause resistance/relapse in patients can also be screened.

The invention may be better understood with reference to the accompanying examples, which are intended for purposes of illustration only and should not be construed in any sense as limiting the scope of the present invention as defined in the claims appended hereto.

Example 1

In order to demonstrate the invention, a microfluidic chip and detector were constructed. The microfluidic chip was fabricated using two-layer soft lithography. Two different molds were first fabricated by a photolithographic process to create the fluidic channels and the control channels that actuate the values located in the top and bottom layers, respectively, of the PDMS-based chip. The fluidic channel mold was made by a three-step photolithographic process. Both round-profile and square-profile channels were created to interface with fully closing regular valves and sieve values, respectively. Upon closure of the valve, round-profile channels close completely while square-profile values leave a small gap near the right-angle.

In the first photolithographic step, a 45-µm thick negative photoresist (SU8-2025) was spin coated on to a silicon wafer (Silicon Quest, San Jose, USA). After UV exposure and development, a square-profile channel pattern was obtained to generate sieve valve channels with a width of 200 µm and height of 45 µm.

In the second step, through the same process, a second layer of 80-µm thick negative photoresist (SU8-2100) was generated on the same wafer to construct the bead columns and circulation chambers with a square-profile channel width of 400 µm and height of 80 µm.

In the third step, a 35-µm thick positive photoresist (AZ 100XT PLP) was spin coated on the same wafer to generate the isolation valve round-profile channels with a channel width of 200 µm and a final height of 45 µm (see below). Each alignment was conducted on a Karl Suss aligner (Karl Suss America Inc., Waterbury, Vt.) to ensure a good match between layers prior to the UV exposure. Once the positive photoresist was developed, the wafer was heated above the glass transition temperature of the positive photoresist. It is through this process that the surface profile of the patterned positive photoresist is transformed into a round-profile channel (for fully closing regular values) while the profile of the negative photoresist remains unchanged (square profile for sieve values). As a consequence, the 35-µm thick positive photoresist square-profile channel results in a 45-µm round-profile channel. The control channel mold was made by fabricating a 30-µm negative photoresist (SU8-2025) pattern on a silicon wafer. In order to achieve reliable performance of each valve, the width of the control channel was set at 250 µm (30 µm height) in sections where the valve modules are located.

Before fabricating the device, both the fluidic and control molds were exposed to trimethylchlorosilane (TMSCl) vapor for 2-3 minutes. Well-mixed PDMS (GE, RTV 615 A and B in 5:1 ratio) was poured onto the fluidic mold located in a Petri dish to give a 5 mm-thick fluidic layer. Another portion of PDMS (GE, RTV 615 A and B in 20:1 ratio) was spin-coated onto the control mold (1,800 rpm, 60 s, ramp 15 s) to obtain the control layer. The thick fluidic layer and thin control layer were cured in an 80° C. oven for 25 and 15 minutes, respectively. Instead of the commonly used 10:1 (A:B) ratio, the two ratios above were found to be the best condition for enhancing the adhesion between the two PDMS layers, as the partially solidified A in the control layer (A:B=20:1) continues to react with excess component B in the fluidic layer (A:B=5:1) when they are interfaced. After incubation, the thick fluidic layer was peeled off the mold, and holes were punched into the fluidic layer for access of reaction solutions. The fluidic layer was then trimmed, cleaned and aligned onto the thin control layer. After further baking at 80° C. for 60 minutes, the assembled layer was peeled off the control mold, and another set of holes were punched for access to the control channels. These assembled layers were then placed on top of a glass slide that was spin-coated (6,100 rpm, 60 s, ramp 15 sec) with PDMS (GE RTV 615 A and B in 20:1 ratio) that had been oven cured for 10 minutes. The device was completed by overnight curing at 80° C.

The pneumatic control setup in this embodiment consisted of 4 sets of eight-channel (eight-valve) solenoid-regulated manifolds controlled through a BOB3 breakout integrated circuit controller board (Fluidigm, San Francisco). Compressed air passed through a gas purifier (Hammond Drierit, Xenia, Ohio) provides pressure (30 psi) to the manifolds. A total of 25 control lines from the device are individually connected to the corresponding channels on the solenoid manifolds with stainless steel tubes (23 Gauge, New England Small Tube Corp, Litchfield, N.H.) using Tygon microbore tubing (Cole-Parmer East, Bunker Court, Calif.).

When a channel on the manifold is activated, air enters the control line connected to the specific channel, providing pressure to close valves in the microfluidic device. The computer control interface incorporates a digital I/O card (AT-DIO-32HS National Instruments, Austin, Tex.) that digitally controls the switching of manifolds through the BOB3 breakout controller board, and the LabVIEW software program that allows manual control of individual valves and automation of the pumping.

The raw images of the position sensitive avalanche photodiode (PSAPD) have inherent spatial distortions. A radioactive printout with a known spatial pattern was used as a calibration tool to image these distortions which were then corrected using an inverse mapping method to arrive at the final spatially corrected image. The PSAPD devices are intrinsically designed for detection of visible light. Therefore, the top surface of the PSAPD was optically passivated with a 9 µm layer of Mylar coated with 3.3 µm of aluminum to allow operation under room light. For each experiment a sacrificial 3 µm Mylar layer was used to protect the passivation layer and the PSAPD detector.

Example 2

In order to prove the concepts of the invention, a microfluidic chip and detector were constructed and an assay scheme was selected to measure small molecule kinases enzymatically phosphorylating small molecule substrates, such as hexokinase phosphorylating glucose or its derivatives. The first application was for nucleoside analog phosphorylation, specifically the phosphorylation of the deoxycytidine analog $^{18}$F-FAC by deoxycytidine kinase (dCK). Nucleoside kinases were selected to illustrate the methods because they are important biomarkers in cancer diagnostics and treatment. One important function of these kinases is the activation of certain classes of anticancer and antiviral prodrugs. They can be also useful in phenotyping cancers based on state of proliferation (thymidine kinase 1, TK1), as well as, their potential resistance to treatment (deoxycytidine kinase, dCK). One method to determine the activity of these enzymes is though a kinase assay, where the rate of phosphorylation of a specific substrate (a nucleoside analog) is measured. The adaptation of the kinase assay to microscale greatly enhances the diagnostic usefulness of this assay through advantages such as the need for less material (no need for full biopsies), faster readout, and automation.

Other assays that were explored included measuring thymidine kinase activity (cell lysates from cells over expressing sr39tk or tk2) using $^3$H-PCV as the substrate.

The integrated microfluidic chip in this example was fabricated using an established two-layer soft lithography process and was controlled using pneumatic manifolds digitally instructed through a computer interface.

The "beta camera" quantitative radioactivity imaging sensor included a position sensitive avalanche photodiode (PSAPD) silicon semiconductor device with an active area of 14×14 mm$^2$ (Model P1305-P; RMD Radiation Monitoring Devices, Watertown, Mass.), custom electronic readout circuitry, and a computer based data acquisition card driven by LabVIEW image acquisition software (National Instruments). Charged particles that interact within the depletion region of the PSAPD convert a portion of their kinetic energy into electron-hole pairs. The PSAPD is operated at high voltage reverse bias (+1750 V) which accelerates the electron-hole pairs and amplifies the signal by 1,000 fold through an avalanche effect. The PSAPD readout uses a five channel output with four position channels and one sum channel. The relative amplitudes of the four position channels are used to determine the location of signal along 2 dimensions. The imaging system also included a CCD optical camera and reference points that allow for spatial co-registration of the beta camera radioactivity images with a photographic image of the microfluidic chip.

To allow the operation of the beta Camera detector under normal room light, the PSAPD was sealed on the top surface with two layers of a metalized Mylar film. Each layer consisted of a Mylar film (3 µm thick) coated with a thin layer of Aluminum (0.2 µm thick). An additional Mylar film is used as a protective sacrificial layer and disposed of in between experiments. The chip can be used to incubate live cells or lysate-based enzymatic reaction products with a substrate layer to control the flow of solutions in the channels above. The microfluidic chip sat on top of a 3 µm thick sacrificial Mylar layer to protect the PSAPD top surface. The PSAPD along with the readout electronics was enclosed inside a metal box with the top surface detector exposed.

Cellular lysates containing the enzyme kinase were incubated with the radio-labeled substrate ($^{18}$F-FAC). Phosphorylation of the substrate molecule results in the addition of a negatively charged phosphate molecule, such that the reaction product (phospho-$^{18}$F-FAC) carries this net negative charge. In the subsequent substrate capture step, the phosphorylated reaction products are captured based on their negative charge using microbeads coated with a weak anion exchanger. In particular, TMA (trimethylamine) conjugated polystyrene beads were used (Macrosphere). TMA is positively charged so the beads function as an anion exchanger. The diameter of the beads is 6 µm. The unphosphorylated substrate is washed away during the binding and washing steps, and the bound phosphorylated substrate remained and was quantified.

Example 3

In order to further prove the concepts of the invention, microfluidic in vitro kinase radio assay (µ-ivkra) using BCR-ABL oncogenic kinase-positive leukemia samples was produced. A polydimethylsiloxane (PDMS)-based integrated microfluidic chip that performs an immunocapture-based kinase assay was fabricated with an integrated position sensitive avalanche photodiode detector (PSAPD) to function as a camera for imaging charged beta particles as a radioactivity-based readout for the assay. The beta camera allowed real-time monitoring of the radioactivity distribution during the assay, and quantified the final amount of radioactivity incorporated into the substrate. Control and readout of the microfluidic device and beta camera were performed via custom electronics and a personal computer. The resulting device performs an automated multi-step kinase reaction assay with coupled readout in a single unit, complete from sample loading to final quantitative data.

The cell lines that were used were Pro-B, lymphoid, Ba/F3 cells transformed with BCR-ABL (p210 isoform) that were provided by Charles Sawyers (UCLA). These cells display similar levels of BCR-ABL expression and signaling as patient leukemia primary samples that are positive for the Philadelphia chromosome (Ph+), the chromosomal translocation that results in expression of the BCR-ABL fusion protein. The K562 (Ph+) and U937 (Ph−) human leukemic cell lines were provided by John Colicelli (UCLA). BCR-ABL expression (or lack of expression) was verified by the presence (or absence) of a 210 kDa anti-c-ABL reactive protein (p210 BCR-ABL isoform; antibody clones K-12, Santa Cruz Biotechnology and OP20, EMD Chemicals, Gibbstown, N.J.) and elevated (or baseline) pan-specific anti-phosphotyrosine levels (clone 4G10, Millipore, Temecula, Calif.). Cells were maintained in RPMI 1640 (Cellgro, Mediatech Inc, Manassas, Va.) with 10% fetal bovine serum (Omega Scientific, Tarzana, Calif.). Cells were lysed in mRIPA buffer (10 mM Beta-glycerophosphate, 50 mM Tris pH 7.4, 1% NP-40, 0.25% Na deoxycolate, 1 mM EDTA, 150 mM NaCl, 1 mM Vanadate, with freshly added 1 mM PMSF, 20 µg/ml leupeptin, 20 µg/ml aprotinin).

Human leukemia patient samples were obtained. Primary cells from the peripheral blood or bone marrow of pre-B-cell acute lymphoblastic leukemia (pre-B-ALL) patients were injected into sublethally irradiated (250 cGy) immune-deficient NOD/SCID mice and serially passaged no more than 3 times. The human leukemia cells create a leukemia-like disease burden in the mice and become the dominant subpopulation in the bone marrow, peripheral blood, and spleen. Disease burden was monitored by measuring the percent of human leukemic cells in the peripheral blood or spleen using hCD45 flow cytometry. Spleen samples were collected by immediate lysis of scalpel-dissected spleen cells in mRIPA buffer using the frosted ends of glass slides to promote cell dissociation, on ice. The human cells in the Ph+ samples were uniformly Ph+ based on cytogenetics. The Ph− sample was a pre-B-ALL with normal karyotype.

Off-Chip And On-Chip In Vitro Kinase Radio Assays were performed for comparison. In vitro kinase assays were performed using established protocols for bead-based immunoaffinity capture of a specific kinase followed by kinase reactions in the presence of a kinase-specific peptide substrate and $^{32}$P labeled ATP. The microfluidic on-chip assay was developed using reagents that were compatible and efficient in the context of microfluidic channels and valves. For the microfluidic assay, 0.1% n-dodecyl-beta-D-maltoside (DDM) was added to all buffers to prevent bead clumping (indicated by /DDM in the buffer name). 0.1% DDM had no detectable effect on BCR-ABL kinase activity. For BCR-ABL kinase immunocapture, the off-chip assay used agarose protein NG beads (40-160 µm; Pierce, Rockford, Ill.) and the on-chip assay used smaller and more sturdy Protein G polystyrene beads (6.7 µm; Spherotech Inc., Lake Forest, Calif.). The large average size and fragility of the agarose beads precluded their use on-chip, and the small size of the polystyrene beads made them impractical for the pipeting-based off-chip assay. Both bead types were coated with anti-c-ABL antibody (OP20, EMD Chemicals).

Off-chip assays were performed using 400 µl (20 µg/µl, or 4×10$^7$ cell equivalents) of cell lysate, and on-chip assays used the amounts indicated in the figure legends. Abltide-biotin conjugate peptide was used as substrate (Millipore), and following the reaction the radio-labeled and unlabeled peptide was captured in off-chip assays using SAM2 Biotin Capture Membrane squares (Promega, Madison, Wis.) or in the on-chip case using streptavidin-coated polystyrene beads (6.7 µm; Spherotech Inc.).

Figure 2:
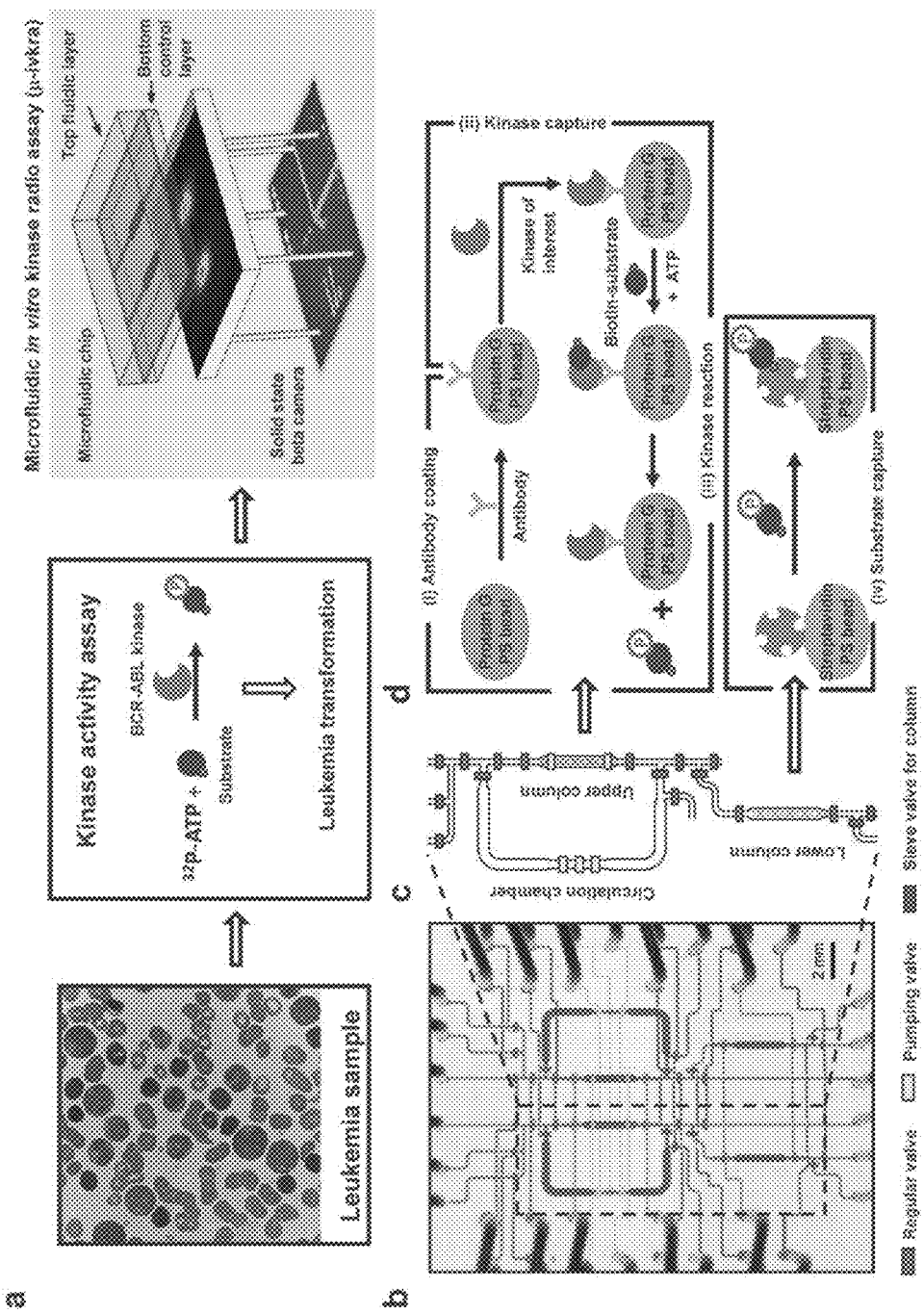
Figure 3:
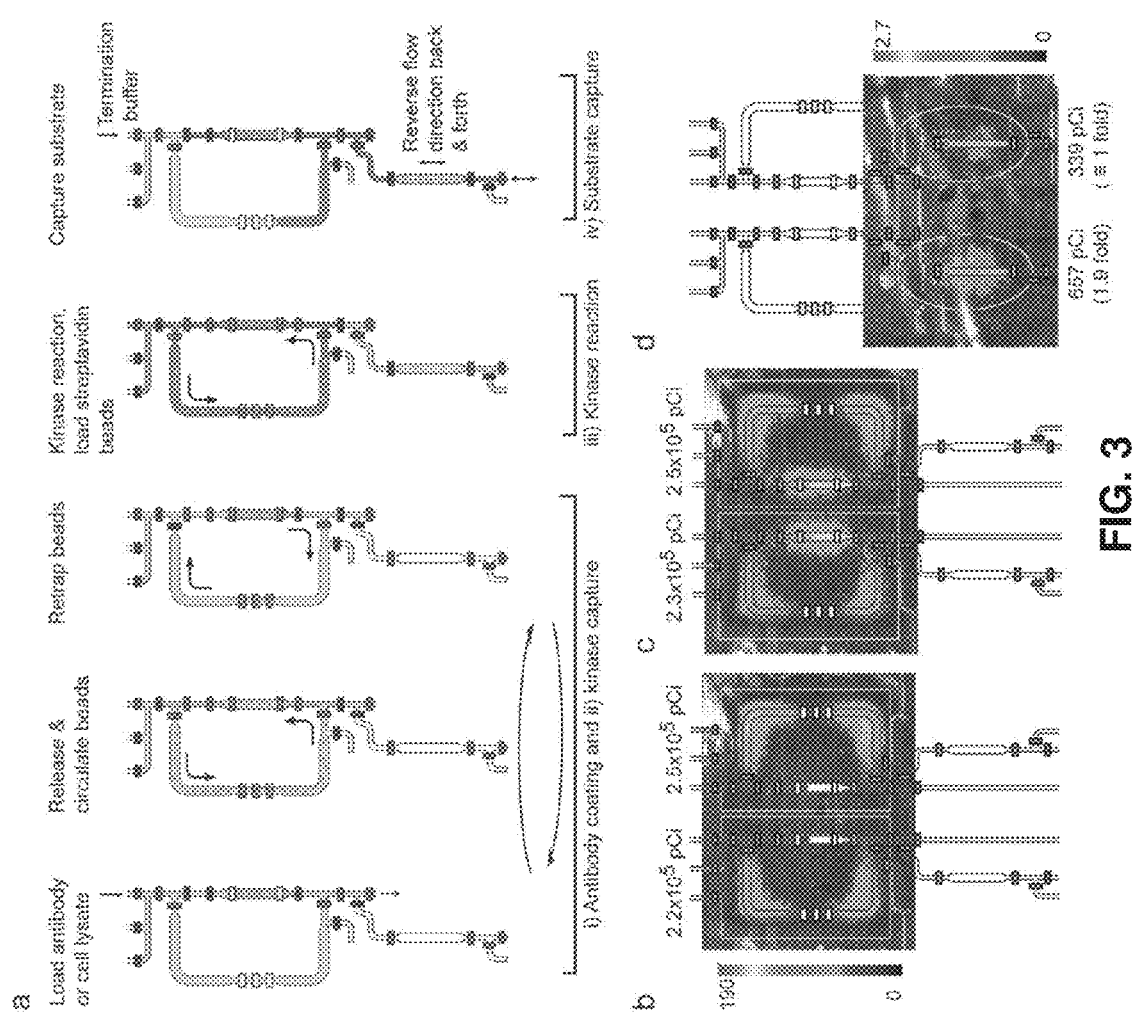
Figure 4:
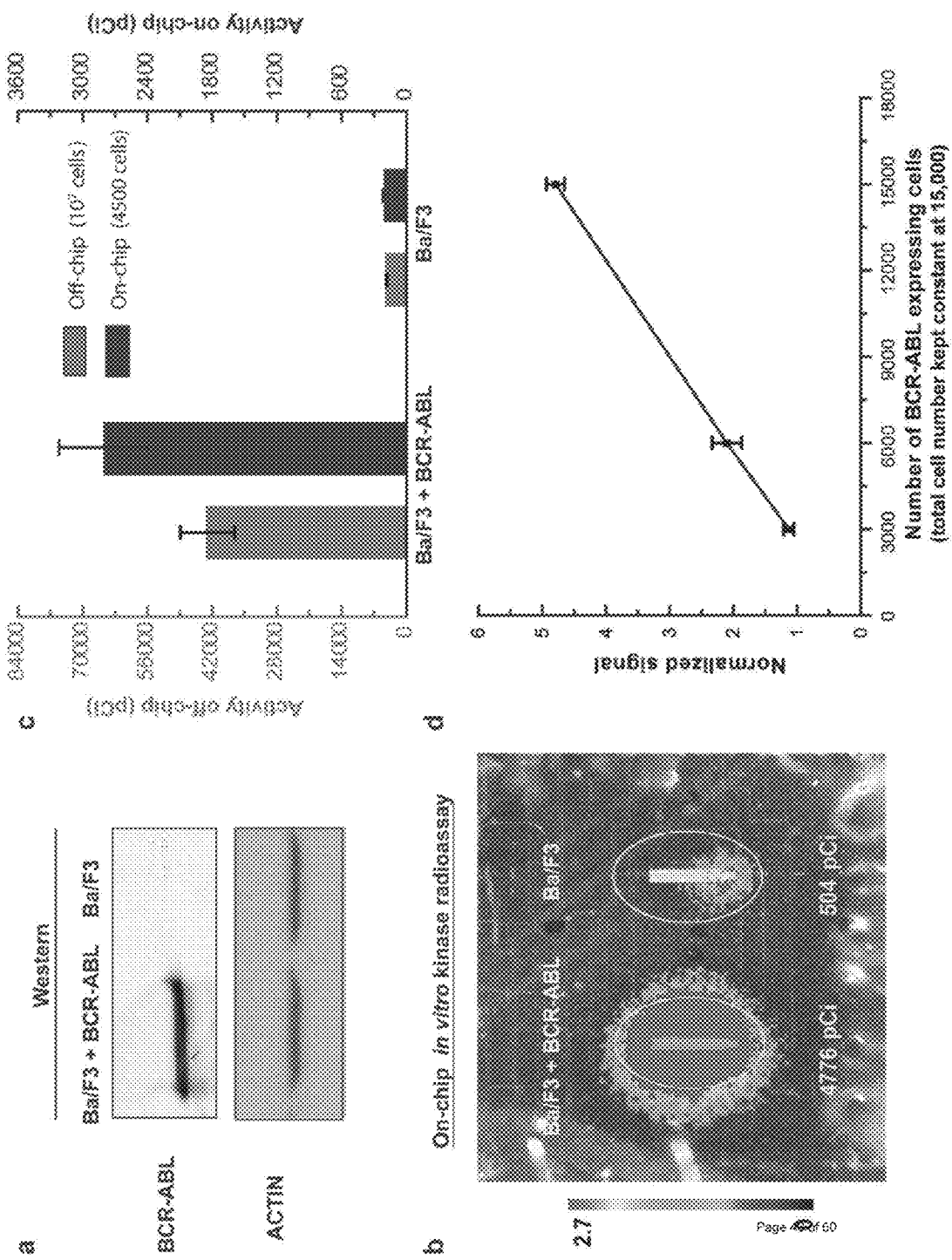
Figure 5:
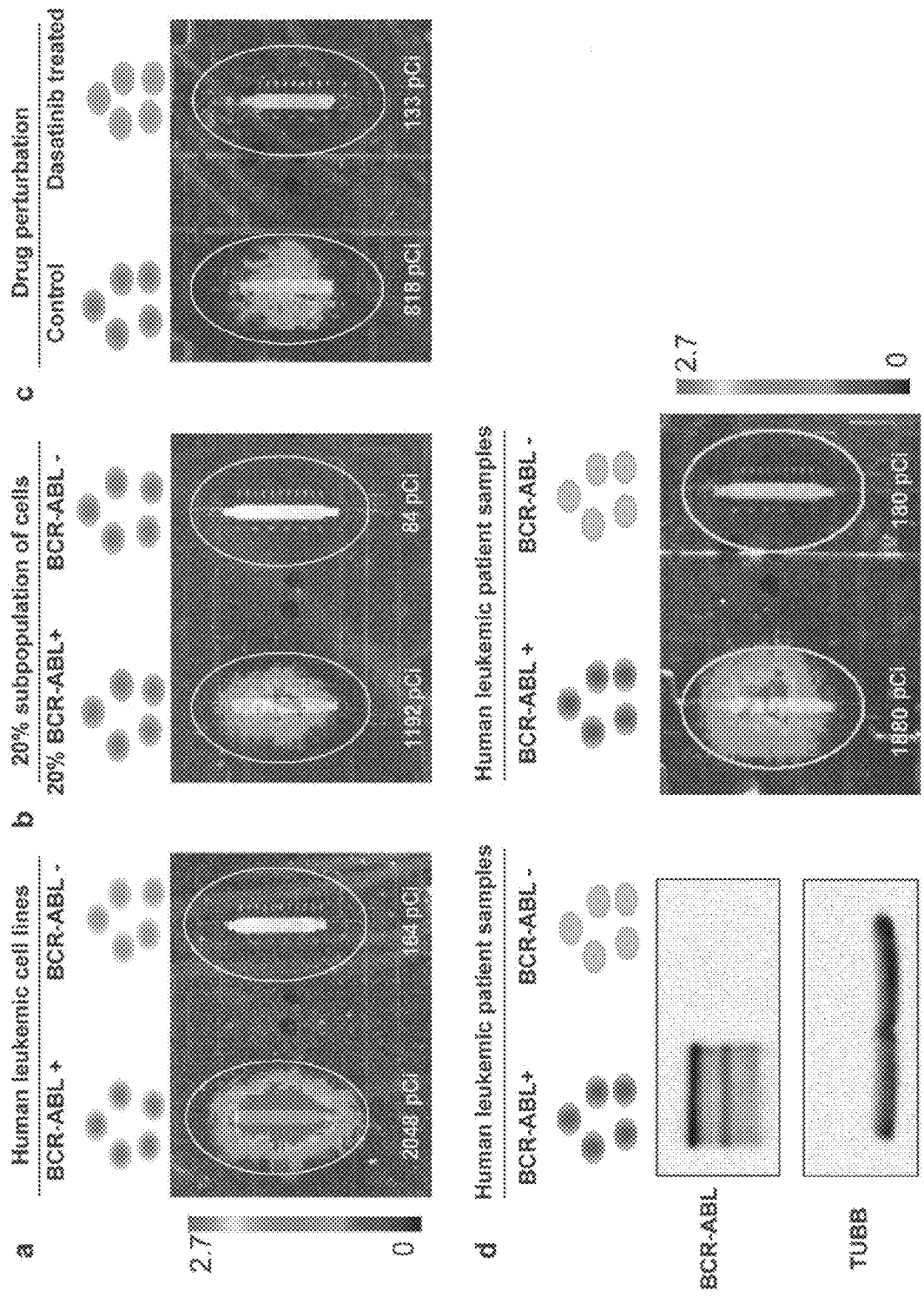

Turning now to FIG. 2 and FIG. 3, the kinase activity assay and microfluidic chip structure are schematically shown. FIG. 2a shows a leukemia smear from a BCR-ABL-driven chronic myelogenous leukemia (CML) patient. In the kinase activity assay the radio-labeled phosphate from $^{32}$P-ATP is transferred to a peptide substrate and the kinase activity is quantified based on isotope incorporation as seen in the center panel of FIG. 2a. The configuration of one embodiment of the (μ-ivkra) assay device is shown in FIG. 2b.

The chip design shown in FIG. 2b contains two isolated and symmetric fluidic modules for individual kinase reactions to run in parallel. The fluidic layer channels of both modules are simultaneously controlled by the pressure actuations of their shared bottom control layer—specifically, each bottom layer control channel regulates a valve in one fluidic module, crosses the midline of the device, and also regulates the corresponding valve in the second module in this embodiment. As diagrammed in FIG. 2c, each module has both i) an upper circulation chamber and bead-trapping upper column for the immunocapture and kinase reaction steps and ii) a lower bead-trapping column for the final substrate capture step. The upper circulation chamber is designed for manipulating the immunocapture beads through multiple trap and release steps as illustrated in FIG. 3.

The microfluidic chip provides two symmetric, isolated reaction units under synchronous digital control. The two layer microfluidic chip has a top fluidic and a bottom control layer. The design includes microfluidic channels in the top layer and in the bottom control layer there are regular isolation valves, sieve valves to trap beads, and peristaltic pump valves for driving fluidic circulation. The microfluidics platform is directly coupled to a highly sensitive charged particle camera (beta camera, PSAPD), enabling on-chip measurements of radioisotope-based kinase assays.

Generally, the assay of FIG. 2d uses protein G-conjugated beads that are loaded into the chip that are coated with anti-ABL antibody and used to capture BCR-ABL kinase from cellular lysates. The captured kinase is then incubated with $^{32}$P-ATP and peptide substrate for the kinase reaction. These steps require three sieve valve-mediated cycles of bead trapping, release and resuspension for the required solution exchanges and a final re-trapping of the immunocapture beads illustrated in FIG. 3a. In the two-layer integrated PDMS microfluidic platform embodiment, it was found that the polystyrene beads were rigid enough for use in conjunction with the microfluidic valves, and that 6.7 μm diameter beads could be readily trapped behind sieve-style valves and subsequently released and re-suspended homogenously. When closed, the sieve values block most of the channel cross-section and thus block bead passage, yet liquid can flow through the remaining opening in the sieve valve.

For the bead trapping and re-mixing steps, care was taken to prevent bead clumping and subsequent clogging of the channels. To avert clumping the device, two sets of imbedded peristaltic pump valves per chamber were used to drive mixing and a pumping protocol with a 2.5 Hz pumping frequency with reversal of the pumping direction every 80 seconds and a mild surfactant (0.1% n-dodecyl-beta-D-maltoside (DDM)) in the solutions was used.

At the end of the assay, the kinase reaction mixture is passed through a lower substrate-capture column. This column was pre-loaded with 6.7 μm streptavidin-coated polystyrene beads to capture the $^{32}$P-labeled (and unlabeled) biotin-conjugated peptide substrate while washing away unincorporated radioisotope ($^{32}$P-ATP) (FIG. 3a, step iv). This single use column is kept homogeneous using a flow reversal protocol that promotes efficient capture of the peptide substrate. The flow protocol involves passing the peptide substrate-containing liquid through the bead column in both directions alternatively three times, followed by washing. For this step the pumping is driven by the non-column peristaltic pump in the upper circulation chamber using a pumping frequency of 5 Hz, and the adjoining chip channels are used as reservoirs during the flow reversals. Upon peptide substrate capture in the lower column, the microfluidic steps of the assay are complete and the $^{32}$P incorporated into the peptides is quantitatively measured using the beta camera.

A schematic of the core steps in the microfluidic in vitro kinase radio assay is illustrated in FIG. 2d: (step i) antibody capture using protein G-conjugated polystyrene (PS) beads (6.7 μm in diameter), (step ii) kinase capture using antibody-coated beads, (step iii) kinase reaction, and (step iv) biotin-labeled peptide substrate capture using 6.7 μm diameter streptavidin-coated polystyrene beads. Steps i-iii are performed in the upper column and circulation chamber where beads can be trapped in the column, released into the circulation chamber (370 nL volume each), mixed to homogeneity, and re-trapped multiple times. The sieve value-mediated bead trapping approach facilitates solution exchange and bead washing. Capture of substrate (step iv) and washing of unincorporated radioisotope ($^{32}$P-ATP) occurs in the lower column prior to quantitative radiometric detection imaging using the beta camera.

Following the scheme shown in FIG. 2d, Protein G-conjugated polystyrene beads (6.7 μm; Spherotech Inc., Lake Forest, Calif.) were washed twice and resuspend in 50 μl wash/TX/DDM buffer. All microfluidic chip columns were pre-washed with wash/TX/DDM buffer. The pre-washed Protein G beads were loaded into the microfluidic chip filling ⅘th of the upper column (80 nL). Three incubation steps with circulation were performed sequentially. For antibody coating, pre-washed beads were incubated with 20 μg/ml anti-c-ABL antibody in wash/TX/DDM buffer for 30 min at room temperature (RT). For kinase capture, either undiluted (20 μg/μl) or lysis buffer diluted cell lysate was incubated with the antibody-coated beads for 30 min at RT. During the bead re-trapping and washing steps, the microfluidic chip was cooled by placing it on ice. For the kinase reaction, a mixture of 2.5 parts kinase wash/DDM buffer, 2.5 parts kinase assay/DDM buffer (containing 40 μM cold ATP, or 1.5 μM for drug inhibition experiments), 1 part [γ-32P] ATP stock (5 μCi/μL, 3 Ci/μMole, 1.7 μM), 6 parts Abltide-Biotin peptide substrate (50 μM, or 200 μM for linearity experiments) was incubated with the kinase coated beads for 15 min at RT. In each step, the new solvent was loaded into the circulation chamber (370 nL) while the beads were trapped in the upper column. The beads were then released and mixed to homogeneity using the circulation pumping protocol with flow reversal every 80 seconds to prevent bead clumping. Between the first and second incubations the beads and circulation chamber were washed with blocking/DDM buffer, and between the second and third incubations they were washed with kinase wash/DDM buffer. The beads were washed by flowing the wash solvent through the loosely packed trapped beads. Equal loading of the radiolabeled ATP was verified by collecting a 1 minute image using the beta charged particle camera. During the last incubation, the lower chamber was washed with Bind & Wash/DDM buffer and loaded with streptavidin-coated polystyrene beads (6.7 μm; Spherotech Inc.) that had been prewashed and re-suspended in Bind & Wash/DDM buffer. The kinase reaction was terminated and the substrate was captured on the streptavidin beads by using a 75 mM $H_3PO_4$ solution to push the substrate containing liquid through the lower column using a flow reversal protocol. The streptavidin beads were washed with 75 mM $H_3PO_4$, and the chip was quantitatively imaged using the beta camera (20 min acquisition).

The sequence of the assay steps shown in FIG. 2d through the microfluidic chip is illustrated further in FIG. 3a. The upper circulation chamber is designed for manipulating the immunocapture beads through multiple trap and release steps (FIG. 3a, steps i-iii). In FIG. 3a, the Roman numerals correspond to the steps in FIG. 2d (steps i-iv). Loading anti-kinase antibody solution or cell lysate into the circulation chamber (370 nL volume). Releasing protein-G beads (6.7 µm diameter, polystyrene) into the circulation chamber for antibody coating (30 min at room temperature (RT)) (step i) or kinase capture (30 min, RT) (step ii). The solution and beads are circulated around the upper chamber driven by two serial sets of peristaltic pump valves. The pumping direction is reversed every 80 sec to prevent bead clumping. Re-trapping beads in the capture column of the upper circulation chamber between steps (5 min) to allow for bead washing and solution exchange in the circulation chamber (step iii) and Kinase reaction with solution and bead circulation in the upper chamber (15 min, RT). The operational steps here are the same as in steps i-ii, except that while waiting for the kinase reaction to finish, the streptavidin polystyrene (PS) beads are independently loaded into the lower column (80 nL volume) from below. (step iv) Capturing and washing the labeled (and unlabeled) peptide substrate in the lower streptavidin bead substrate-capture column using a flow reversal protocol, prior to washing away any unincorporated radioisotope ($^{32}$P-ATP) and using the beta camera (PSAPD) for imaging and quantitation.

FIG. 3b through FIG. 3d illustrate mid-experiment monitoring of device and assay performance and final signal quantitation using the beta camera. Overlaid images of the CCD camera optical image, the false color beta camera radioactivity image, and the chip AutoCAD drawing during various assay steps: (b-c) loaded radioactive ($^{32}$P-ATP) kinase reaction buffer prior to (b) and after (c) circulation demonstrating equal loading, and (d) the final captured radiolabeled peptide substrate in the lower column showing the anticipated 2-fold difference in kinase activity between 6,000 and 3,000 Ba/F3+BCR-ABL cells. The beta camera image scales in counts per second per $mm^2$.

The spatial distribution of the emitted $^{32}$P source is a function of the kinetic energy of the emitted particles, the geometry of the volume containing the isotope (i.e. the microfluidic chamber), and the spatial resolution of the beta camera. The spatial distribution of $^{32}$P for our system can be estimated from the experimental results of the ivkra system. From the beta camera image of the lower substrate-capture columns the spatial distribution of the source signal was measured and a line profile was then drawn across the signal to calculate the full-width tenth-maximum (FWTM). A region of interest (ROI) was then drawn with a width equal to the FWTM of each lower column source in order to count a substantial portion of the emitted signal. Identically sized ROIs were used to measure the radioactivity in the calibration experiments as well as to measure all experimental results from the lower columns.

The geometry of the upper circulation columns required drawing larger ROIs to enclose and measure the emitted signal. The ROIs for the upper chambers of each assay unit were of equal size to ensure that the loading of the radioactive $^{32}$P into each of the upper chambers was approximately equal. No spillover corrections were applied to the measurements. The total detected activity (pCi) for each region of interest ROI was determined.

As indicated previously, the beta camera serves as the radioactivity readout device for the microfluidic kinase assay. The detector in the beta camera was a 14×14 $mm^2$ position sensitive avalanche photodiode (PSAPD) with a very low inherent background count rate (1.5 counts/hour/$mm^2$). Benefits of the PSAPD detector include its monolithic and thus rugged design, and position decoding via a five channel analog readout.

When the PSAPD is placed in close contact with a radioactive source, it has a high avalanche-mediated sensitivity for detecting emitted charged particles. Using known levels of $^{32}$P, a calibration curve was established and the absolute sensitivity of the integrated microfluidic beta camera was determined to be 29%. The beta camera itself has high intrinsic sensitivity to $^{32}$P particles that traverse through the PSAPD detection region. The geometric configuration of the integrated microfluidic beta camera device reduces the overall sensitivity due to i) half of the beta particles being emitted away from the planar detector and ii) attenuation of beta particles by the control layer of PDMS material (100 µm) and the glass slide (150 µm) between the microfluidic channel and the beta camera.

The beta camera is position sensitive and therefore a single detector was used for multiple simultaneous readouts from adjacent columns in the configuration shown in FIG. 2b and FIG. FIG. 3b-d. In addition to the final readout, the beta camera can be used for qualitative and quantitative operational checkpoints. For example, during the assay the radioactivity distribution and intensity was monitored in real time to test for uniform chip operation during fluid and bead manipulation. These checkpoints verify equal loading, uniform mixing, proper valve operation and chip channel integrity (FIG. 3b-c and Table 1).

For validation of the On-Chip In Vitro BCR-ABL Kinase Radio Assay, both a traditional off-chip BCR-ABL kinase radio assay and an on-chip kinase assay were performed using the same cell lysates. Anti-ABL immunoblot of the Ba/F3 cell line with and without expression of constitutively active BCR-ABL kinase (loading control, anti-Actin immunoblotting) is shown in FIG. 4a. The results of the on-chip BCR-ABL kinase reaction was performed with 12,000 Ba/F3+BCR-ABL cells (left column) and parental Ba/F3 cells (right column) of FIG. 4b. Final results were represented by an overlay of optical and beta camera false-color images (20 min acquisition) of the lower substrate capture columns. The bar scale (counts per second per $mm^2$) and total detected activity (pCi) for each circled ROI (region of interest) are indicated.

A comparison between traditional test tube-based (off-chip) and on-chip in vitro BCR-ABL kinase radio assays are graphed in FIG. 4c. Off-chip assays were performed with $10^7$ cells and on-chip assays with 4,500 cells. Results reflect absolute quantitation, and the error bars represent the standard deviation for three assays performed on different days using aliquots of the same lysate with different chips.

The Off-Chip In Vitro kinase radio assays for comparison were performed with Protein NG agarose beads (40-160 µm; Pierce, Rockford, Ill.) from 40 µl of slurry were pre-washed twice with 200 µl wash/TX buffer. Washed beads were resuspended with 400 µl of 10 µg/ml anti-c-ABL antibody (OP20, Millipore, Temecula, Calif.) in wash/TX buffer. The beads were coated with antibody overnight at 4° C. with gentle rocking, followed by three washes with 400 µl blocking buffer. The antibody-coated beads were next used to capture kinase from 400 µl (20 µg/µl, or 4×107 cell equivalents) of cell lysate during an 8 hour incubation at 4° C. with gentle rocking, followed by two washes with 500 µl wash buffer and two with 500 µl kinase wash buffer. After washing, the beads were re-suspended in 40 µl kinase wash buffer and warmed to 25° C. 40 µl kinase assay buffer (containing 200 µM cold ATP and 17 nM [γ-32P]ATP (3 Ci/µMole; PerkinElmer, Waltham)) and 80 µl of 200 µM Abltide-biotin conjugate peptide substrate (Millipore) were added to the resuspended beads and the kinase reaction proceeded for 15 min at 25° C. The reaction was terminated with 120 µl 75 mM H3PO4 and incubation on ice for 15 min. 9 µl of each reaction was spotted to SAM2 Biotin Capture Membrane squares followed by washing and quantitation by scintillation counting per the instructions of the manufacturer (Promega, Madison, Wis.). The reaction solution was used to determine the specific activity of hot ATP.

A demonstration of linearity using BCR-ABL expressing Ba/F3 cells is shown in FIG. 4d. In each experiment, samples were diluted with parental non-BCR-ABL-expressing cells as necessary to keep the total cell number constant at 15,000. The graph incorporates data from a total of 16 sample aliquots (8 pair-wise chip experiments performed on different chips using mixed aliquots of the same lysates). The results from each experiment were normalized such that the mean detection signal was set equal to the mean number of cells in the experiment divided by 3000. Non-specific background signal was not subtracted. Thus, the results represent relative quantitation designed to identify the linear region of the platform. The R-squared value from a linear regression fit is 0.997. Error bars represent the standard deviation.

These assays were done using Ba/F3 cells, a pro-B murine cell line, transfected with either a BCR-ABL expression plasmid or an empty vector control (FIG. 4a). The off-chip kinase assay was performed using millions of cells while the on-chip assay required only 4,500 cells. A similar order of magnitude was observed in the 'BCR-ABL versus control' fold-change values between the off-chip (10.2-fold, ±1.2 standard deviation, n=3) and on-chip (14.6±0.7-fold, n=3) assays (FIG. 4b-c), confirming that the on-chip assay was performing correctly. These absolute quantitation assays were performed using the same lysate split into aliquots, and the low standard deviation in fold change and raw radioactivity signal (FIG. 4c) reflects the reproducibility of the assay performed on different days using different chips. The difference in exact fold change between on- and off-chip results is likely primarily due to differences in the unsubtracted background signal between the two assays and its effect on the accurate measurement of the low ABL activity in the BCR-ABL-free control cells.

The linearity of the on-chip in vitro BCR-ABL kinase radio assay was then tested. In these experiments different amounts of lysate from BCR-ABL expressing Ba/F3 cells were loaded into each of the microfluidic chip reaction units (with parental Ba/F3 cell lysate used to dilute the amount of BCR-ABL kinase while keeping the total cell number constant). These relative quantitation experiments demonstrated linearity over a 5-fold range of input as seen in FIG. 4d. The lower limit was due mainly to non-specific background signal from radioisotope bound to the streptavidin beads (the beta camera itself has very low inherent background). Future device designs may use smaller volumes of capture reagents to reduce the background, and incorporate additional reaction units to allow direct determination and subtraction of background to extend this linear range.

The apparatus was also able to detect autophosphorylation of BCR-ABL bound to the antibody-coated beads in the upper kinase reaction module at the end of the kinase reaction. During the development of the assay this readout was used to verify that the reaction had proceeded as anticipated with stronger signal coming from the sample with higher BCR-ABL levels.

The two 30-min binding steps of the on-chip assay are shorter than those used in conventional immunocapture-based kinase radio assays, which are often reported as from 1-4 hours to overnight. In total, the on-chip assay can be completed in 4 hours. Only 1 hour elapses from lysate addition to the end of the kinase reaction, thus reducing the potential for decay of kinase activity. This and other advantages of the microfluidic platform, such as efficient, immediate and consistent mixing, improve the net on-chip kinase activity efficiency by approximately an order of magnitude compared to off-chip assays performed with the same lysates (Table 2).

Example 4

In order to demonstrate the microfluidic assay of the invention on different leukemic systems, the apparatus described above was adapted to other BCR-ABL-expressing leukemia systems. The device was able to detect substantial BCR-ABL kinase activity differences between patient-derived leukemic cell lines with endogenous BCR-ABL expression (K562) compared to leukemic cell lines without BCR-ABL expression (U937).

Detection of BCR-ABL activity from BCR-ABL expressing human cell lines is shown in FIG. 5a-c. The on-chip in vitro BCR-ABL kinase radio assay was performed on lysates from the human leukemic cell line K562 (with leukemia patient derived BCR-ABL expression) and U937 (with no BCR-ABL expression).

FIG. 5b depicts the qualitative detection of BCR-ABL activity from a subpopulation of BCR-ABL expressing cells as a model for heterogeneous patient samples. BCR-ABL activity was detected from a 1 in 5 subpopulation of BCR-ABL expressing cells (4,500 Ba/F3+BCR-ABL: 18,000 Ba/F3 cells versus 22,500 Ba/F3 cells). Detection of sensitivity to BCR-ABL-targeted drug inhibition is shown in FIG. 5c. Ba/F3+BCR-ABL (p210) cells were treated with 125 nM dasatinib or DMSO solvent alone (control) for 2 hours and then BCR-ABL kinase activity was measured in the microfluidic platform (4,500 cell input).

The detection of BCR-ABL activity from Ph+ leukemic patient samples in a mouse xenograft system results are shown in FIG. 5d. Mouse spleens with more than 95% hCD45 Ph+ cells or more than 90% hCD45 Ph− cells were harvested, lysed and analyzed by anti-c-ABL immunoprecipitation and immunoblotting and anti-TUBB immunoblotting (left) and by the on-chip in vitro BCR-ABL kinase radio assay (4,500 cell input) (right). All results are represented by overlays of optical images of the lower substrate capture columns and beta camera false color images (20 min acquisition). The bar scale (counts per second per $mm^2$) and total detected activity (pCi) for each circled ROI are indicated. The size of the ROI was uniform across all experiments.

Since leukemic patient samples are often 'contaminated' with normal cells that do not have elevated kinase activity, the possibility of measuring the BCR-ABL kinase activity from a subpopulation of BCR-ABL-expressing cells was tested. A 1:4 mixture of BCR-ABL- to non-BCR-ABL-expressing cells using the Ba/F3 system was used. The signal from this 20% BCR-ABL-expressing subpopulation was clearly detectable and distinct compared to the background signal from a control non-BCR-ABL-expressing population (FIG. 5b).

One potential application of the on-chip radioactive in vitro kinase assay is to measure the inhibition of kinases by molecularly targeted therapeutics directly on patient and animal model samples. To demonstrate this use, BCR-ABL-expressing Ba/F3 cells were treated with 125 nM dasatinib, a well-known BCR-ABL inhibitor, and then the BCR-ABL kinase activity from 4,500 cells was measured. Upon treatment, the BCR-ABL activity was inhibited substantially, with the detected assay signal reduced to background levels (FIG. 5c).

Finally, the microfluidic platform was tested for detecting BCR-ABL kinase activity from clinical samples. For this test, pre-B-cell acute lymphoblastic leukemia (pre-B-ALL) primary patient cells were used that were both positive and negative for the Philadelphia chromosome (Ph) and thus also for BCR-ABL protein. These patient cells were injected into NOD/SCID mice in which they proliferate to create a leukemia-like disease burden. Ultimately the human leukemic cells make up the vast majority of the peripheral blood, bone marrow and spleen cells. Fresh spleens from these leukemia-burdened xenograft mice were processed and loaded onto the microfluidic platform to measure BCR-ABL kinase activity. Signal comparable to our cell line results was obtained from the Ph+ patient samples, while the negative control Ph− samples had only background levels of signal (FIG. 5d).

Taken together, the reduced sample input, decreased assay time, and digitally controlled reproducibility of the microfluidic kinase radio assay facilitates direct experimentation on clinical samples that are either precious or perishable. This potential is demonstrated using a patient sample and mouse xenograft system. Other applications include profiling of patient and animal model samples for their kinase inhibitor drug sensitivity, or measurement of kinase activity from stem cells, cancer stem cells, rare immune cells and other subpopulations, for example following flow cytometry- or microfluidic-based sorting.

Example 5

Concentrations of on-chip substrate can be optimized. In determining the substrate concentration for the on-chip reaction, we optimized between i) the higher reaction velocity when the substrate concentration is higher and ii) the streptavidin beads having a finite binding capacity. Note that the streptavidin beads bind both the substrate and product, since the beads bind the biotinylated peptide independent of its phosphorylation state. The binding capacity of the streptavidin beads was measured by measuring the fraction of captured reaction product compared to product that flowed through the column using liquid scintillation counting. From these results the binding capacity was estimated as 5 nMoles of biotinylated peptide per column of packed streptavidin beads (80 nL). The relative on-chip signal for different concentrations of substrate is thus proportional to the product of the reaction velocity and the fraction of substrate captured represented by:

$$\alpha \text{ velocity} \times \text{fraction captured} = \frac{V_{max} \times [\text{substrate}]}{K_m + [\text{substrate}]} \times \frac{\text{binding capacity}_{streptavidin\ beads}}{[\text{substrate}] \times \text{volume}_{circulation\ chamber}}$$

Figure 6:
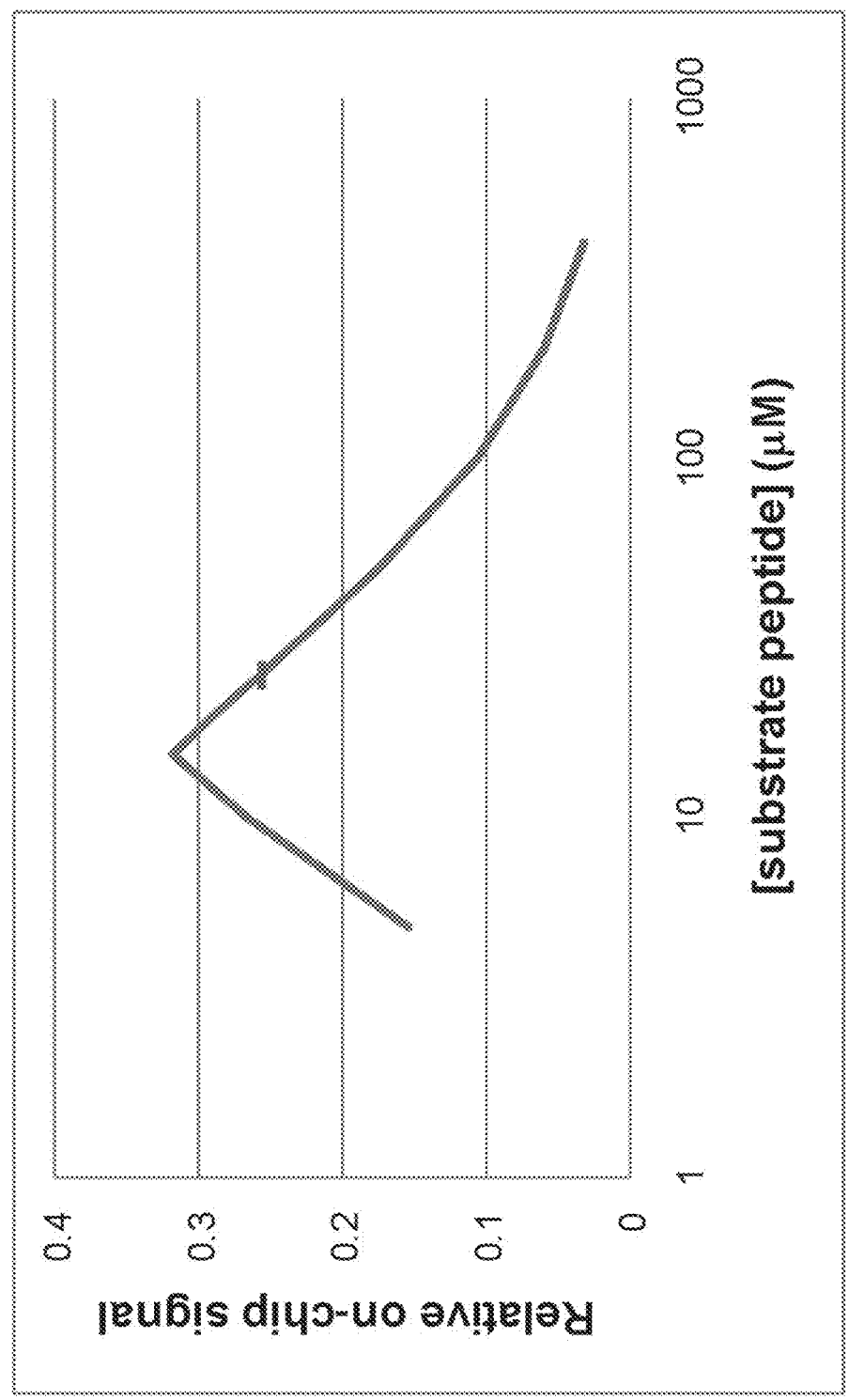
FIG. 6 is graph of the optimization of on-chip substrate concentrations.

The graph of FIG. 6 plots this formula for $K_m$=27.6 µM (1), binding capacity$_{streptavidin\ beads}$=5 nMoles, and volume$_{circulation\ chamber}$=370 nL. We chose to use a 25 µM substrate concentration (tick mark on graph) for the majority of our reactions since this is close to maximal signal while keeping the reaction velocity relatively high (0.5×$V_{max}$). At this concentration, a 15 min reaction uses less than 2% of the substrate. Higher concentrations are still practical, as the linearity experiments of FIG. 4d were performed at 200 µM substrate concentration.

Example 6

Figure 7:
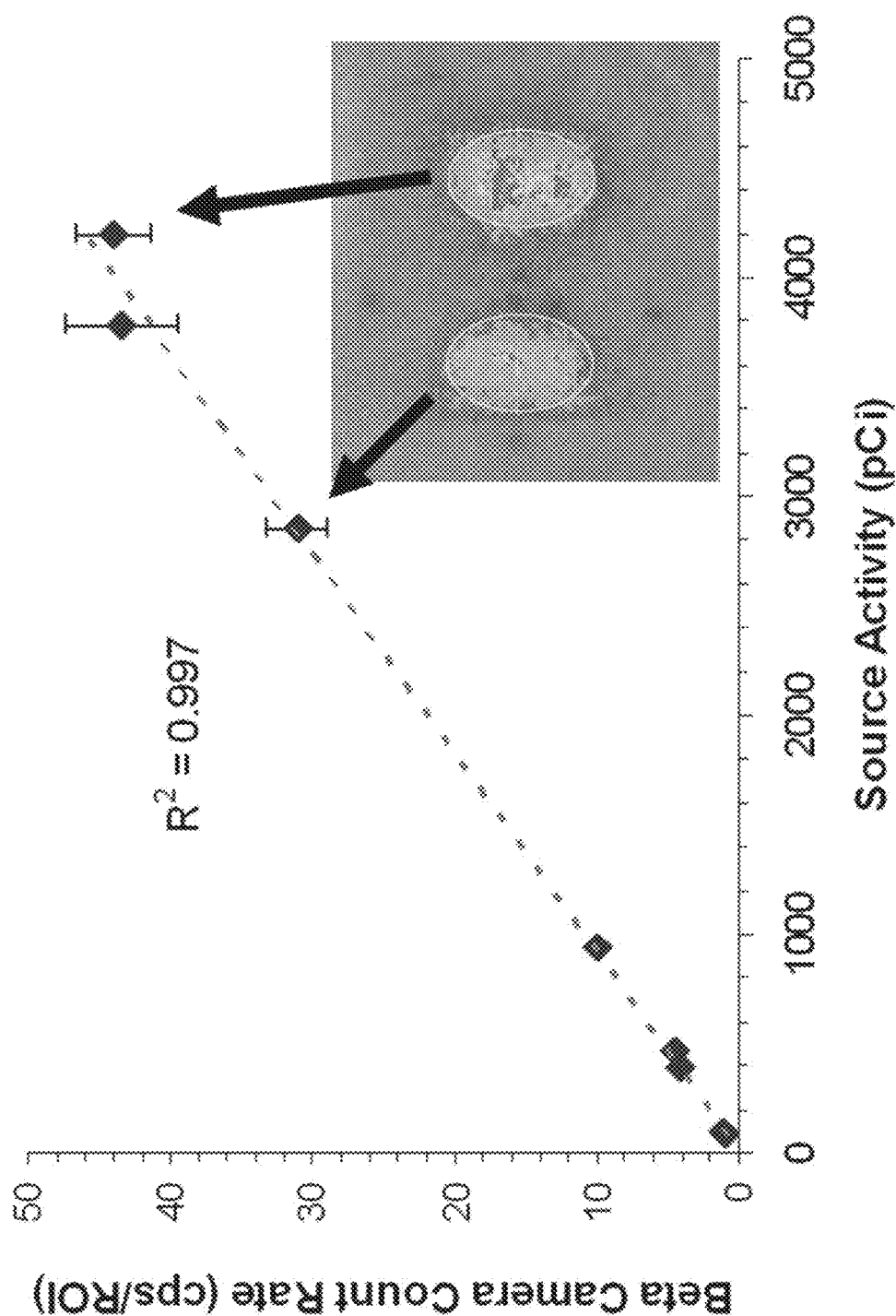
FIG. 7 is a graph for calibration of the µ-ivkra beta camera for detection of $^{32}P$ radionucleotide.

Calibration results of the µ-ivkra beta camera for detection of $^{32}$P radionucleotide are shown in FIG. 7. The calibration graph shows the net counts detected in a region of the beta camera (PSAPD) as a function of the total $^{32}$P activity. A range of $^{32}$P sources were placed with 100 µm of plastic and 150 µm of glass between the source and detector surface in order to replicate the microfluidic chip geometric configuration. A beta camera image of two $^{32}$P sources is shown in the inset. Total detected source activity (counts per second, cps) is plotted for each ROI (region of interest, circled) against the true source activity (pCi, 0.037 decays per second/pCi) as measured using a liquid scintillation counter. The µ-ivkra device has an overall $^{32}$P detection sensitivity of 29% as determined by the slope of the calibration curve. In other words, 29% of decay events occurring in the microfluidic device are detected by the coupled beta camera. The beta camera itself has high intrinsic sensitivity to $^{32}$P particles that traverse through the PSAPD detection region. The geometric configuration of the integrated microfluidic beta camera device reduces the overall sensitivity due to i) the fact that half of the beta particles are emitted away from the planar detector and ii) attenuation from the 100 µm-thick control layer of PDMS material and the 150-µm thick glass slide between the microfluidic bead column channel and the beta camera.

Accordingly, a miniaturized kinase assay that allows for activity measurements from small patient samples is provided using a microfluidic assay platform that is directly coupled to a beta camera for sensitive and quantitative readout of kinase activity via measurement of $^{32}$P incorporation. In addition, a microfluidic in vitro kinase radio assay (µ-ivkra) using BCR-ABL oncogenic kinase-positive leukemia samples was demonstrated. The stand-alone benchtop apparatus can measure kinase activity from as few as 3,000 cells from protein or small molecule substrates and opens new possibilities for diagnostics from minute patient samples from blood draws, bone marrow aspirates and needle biopsies.

From the discussion above it will be appreciated that the invention can be embodied in various ways, including the following:

1. An apparatus for performing a microfluidic radioactivity based assay, comprising a microfluidic chip with a microchannel system and at least one reaction element adapted to capture radioactively labeled molecules; and a solid state radiation detector coupled to the microfluidic chip; wherein radiation emitted from the microfluidic chip is detected.

2. An apparatus as recited in embodiment 1, wherein the reaction element comprises a plurality of reaction columns retaining affinity beads fluidly connected to the microchannel system of the microchip.

3. An apparatus as recited in embodiment 1, wherein the reaction element comprises a plurality of reaction columns retaining surface functionalized beads fluidly connected to the microchannel system of the microchip.

4. An apparatus as recited in embodiment 3, wherein the surface functionalized beads are functionalized with a coating of a plurality of enzyme specific antibodies, wherein enzymes disposed in a liquid flow through the reaction column bind to the antibodies on the surface of the beads.

5. An apparatus as recited in embodiment 4, wherein the surface functionalized beads comprise Protein G polystyrene beads functionalized with a coating of kinase specific antibodies.

6. An apparatus as recited in embodiment 1, wherein the microchannel system further comprises a circulation chamber fluidic circuit fluidly connected to the reaction element with at least two ports; wherein the fluid flow from a first port of the reaction element is circulated through the circulation chamber and back into the reaction element through a second port of the reaction element.

7. An apparatus as recited in embodiment 1, wherein the reaction element comprises a plurality of reaction columns retaining surface functionalized beads fluidly connected to the microchannel system of the microchip; and a circulation chamber fluidic circuit fluidly connected to an entry port and to an exit port of each reaction column; wherein the functionalized beads can be removed from the reaction column to the circulation chamber through the exit port and returned to the reaction column through the entry port.

8. An apparatus as recited in embodiment 1, wherein the microchannel system further comprises at least one second reaction element within a flow path of the first reaction element.

9. An apparatus as recited in embodiment 8, wherein the second reaction element comprises at least one second reaction column retaining affinity beads fluidly connected to the first reaction column; wherein reaction substrates released from the first reaction column are captured by the second reaction column.

10. An apparatus as recited in embodiment 8, wherein the second reaction element comprises at least one second reaction column retaining surface functionalized beads fluidly connected to the first reaction column; wherein reaction substrates released from the first reaction column are captured by the second reaction column.

11. An apparatus as recited in embodiment 1, wherein the radiation detector comprises a position sensitive avalanche photodiode (PSAPD)-based solid state beta camera; wherein beta radiation emissions from the microfluidic chip are detected and quantified by the camera.

12. An apparatus as recited in embodiment 11, wherein the radiation detector further comprises an aluminated Mylar film on a top surface of the radiation detector; and a Mylar sheet coupled to said aluminated Mylar film and the microfluidic chip disposed on a top surface of said Mylar sheet; wherein the radiation detector is shielded from visible light by the aluminated Mylar film and Mylar sheet.

13. An apparatus for performing a microfluidic radioactivity based assay, comprising a microfluidic chip having a microchannel system; a plurality of reaction columns configured to retain surface functionalized beads and adapted to capture radioactively labeled molecules and fluidly connected to the microchannel system; a fluidic control system configured to control fluid flow through the microchannel system and reaction columns; and a solid state radiation detector coupled to the microfluidic chip; wherein radiation emitted from the microfluidic chip is detected.

14. An apparatus as recited in embodiment 13, wherein the radiation detector comprises a position sensitive avalanche photodiode (PSAPD)-based solid state beta camera; wherein beta radiation emissions from the microfluidic chip are detected and quantified by the camera.

15. An apparatus as recited in embodiment 14, wherein the radiation detector further comprises an aluminated Mylar film disposed on a top surface of said radiation detector; and a Mylar sheet coupled to the aluminated Mylar film and the microfluidic chip disposed on a top surface of the Mylar sheet; wherein the radiation detector is shielded from visible light by the aluminated Mylar film and Mylar sheet.

16. An apparatus as recited in embodiment 13, wherein the surface functionalized beads are functionalized with a coating of a plurality of enzyme specific antibodies, wherein enzymes disposed in a liquid flow through the reaction column bind to the antibodies on the surface of the beads.

17. An apparatus as recited in embodiment 13, wherein the surface functionalized beads comprise Protein G polystyrene beads functionalized with a coating of a plurality of a kinase specific antibody.

18. An apparatus as recited in embodiment 13, wherein the microchannel system further comprises a circulation chamber fluidic circuit fluidly connected the reaction column by at least two ports; wherein a fluid flow from the reaction element is circulated through the circulation chamber and back into the reaction element through one or more ports of the reaction element.

19. An apparatus as recited in embodiment 13, wherein the reaction columns comprise a first reaction column fluidly connected to a second reaction column, wherein an output from the first reaction column flows through the second reaction column.

20. An apparatus for performing a microfluidic kinase radioactivity based assay, comprising a microfluidic chip with a microchannel system; a plurality of first reaction columns fluidly connected to the microchannel system configured to retain surface functionalized beads coated with a kinase specific antibody and adapted to allow kinase reactions with at least one radioactive substrate; a second reaction column adapted to capture radioactively labeled molecules, said second column fluidly connected to at least one first reaction column; a fluidic control system configured to control fluid flow through the microchannel system and first and second reaction columns; and a solid state radiation detector coupled to the microfluidic chip; wherein kinases from a sample cell lysate bind to the kinase specific antibodies of the functionalized beads of the reaction columns and are captured; wherein the captured kinases react with at least one radioactive substrate to produce a radioactive reaction product; and wherein radiation emitted from said microfluidic chip is detected.

21. An apparatus as recited in embodiment 20, wherein the second reaction column is configured to retain solid state anion exchange beads.

22. An apparatus as recited in embodiment 20, wherein the kinase is a small molecule kinase.

23. An apparatus as recited in embodiment 20, wherein the kinase is a small molecule kinase selected from the group of kinases consisting essentially of a hexokinase, a thymidine kinase or a deoxycytidine kinase.

24. An apparatus as recited in embodiment 20, wherein the kinase is a protein kinase.

25. An apparatus as recited in embodiment 20, wherein the kinase is a protein kinase selected from the group consisting of BCR-ABL, AKT, EGFR, PDGFR, c-KIT, ALK, ERK, MEK, RAF, FLT3, and IKK.

26. An apparatus as recited in embodiment 20, further comprising a circulation chamber fluidic circuit fluidly connected to an entry port and to an exit port of each first reaction column; wherein a fluid flow from the exit port of the first reaction column is circulated through the circulation chamber and back into the reaction element through the entry port of the first reaction chamber; wherein cycles of bead trapping, release and resuspension permit bead washing and solution exchanges are performed within the first reaction column.

27. An apparatus as recited in embodiment 20, further comprising: a computer and programming operably coupled the fluidic control system and the radiation detector; wherein the control of timing and sequence of fluid flow through the microfluidic chip are controlled by computer programming, wherein radiation detection is controlled and recorded.

28. A method for performing a microfluidic kinase radioactivity based assay, comprising: providing a microfluidic chip with a system of microchannels, one or more valves, a flow control system, a plurality of reaction chambers, at least one circulation chamber and a radiation detector; coating microbeads with a coating of kinase specific antibodies; capturing kinase molecules from a sample cell lysate with the kinase specific antibodies on the microbeads within a first reaction chamber; cycling the coated microbeads with captured kinase molecules from the first reaction chamber through a circulation chamber and back to the first reaction chamber; reacting the captured kinase molecules with at least one radioactively labeled substrate to produce a reaction product; collecting labeled reaction products in a second reaction chamber; and detecting radiation from the collected reaction products.

29. A method for performing a microfluidic kinase radioactivity based assay as recited in embodiment 28, further comprising introducing a kinase inhibitor to the first reaction chamber; reacting the captured kinase molecules with at least one radioactively labeled substrate in the presence of the kinase inhibitor to produce a reaction product; and quantifying the sensitivity of the kinase to the inhibitor.

30. A method for performing a microfluidic kinase radioactivity based assay as recited in embodiment 28, wherein the kinase is a protein kinase selected from the group consisting of BCR-ABL, AKT, EGFR, PDGFR, c-KIT, ALK, ERK, MEK, RAF, FLT3, and IKK.

31. A method for performing a microfluidic kinase radioactivity based assay for screening enzyme and potential enzyme inhibitor combinations, comprising providing a microfluidic chip with a system of microchannels, one or more valves, a flow control system, a plurality of reaction chambers at least one circulation chamber; capturing kinase molecules from a sample cell lysate within a first reaction chamber; cycling the coated microbeads with captured enzyme molecules from the first reaction chamber through a circulation chamber and back to the first reaction chamber; introducing a putative enzyme inhibitor to the first reaction chamber; reacting the captured enzyme molecules with at least one labeled substrate to produce a reaction product; quantifying the reaction products.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Qualitative and quantitative operational checkpoints in the μ-ivkra assay

| Step | Acquisition time | Purpose | Monitored area |
|---|---|---|---|
| After loading kinase reaction buffer | 1 min | Verify equal loading Verify proper chip operation | Circulation chamber & upper bead columns |
| After the kinase reaction | 1 min | Verify homogenous mixing Verify proper chip operation | Circulation chamber & upper bead columns |
| After pumping the reaction solution to the lower columns | 10 min | Monitor flow Check radioactivity background Measure the degree of kinase autophosphorylation | Circulation chamber & upper bead columns |
| After washing the lower streptavidin columns | 20 min | Verify substrate capture Quantify the kinase activity via incorporated radioisotope | Lower bead trapping columns |

Summary of key checkpoints during a μ-ivkra assay. Four checkpoints at different steps in the procedure are used to confirm a successful assay and verify proper physical and operational performance of the device.

TABLE 2

Relative reaction efficiency between on-chip and off-chip kinase assays $$\text{kinase assay efficiency} = \frac{\text{pCi incorporated/specific activity}}{\text{lysate volume} \times \text{reaction time}}$$

| | Off-chip | On-chip |
|---|---|---|
| $^{32}$P incorporated (pCi) * | 103616 | 2797 |
| relative specific activity (relative hot ATP/cold ATP) † | 1 | 33 |
| lysate volume (uL) | 400 | 0.05 |
| reaction time (min) | 30 | 15 |
| efficiency (arbitrary units), normalizing for the factors listed above | 12.3 | 113 |
| relative efficiency, normalizing for the factors listed above | 1 | 13.1 |

TABLE 2-continued

Relative reaction efficiency between on-chip and off-chip kinase assays $$\text{kinase assay efficiency} = \frac{\text{pCi incorporated/specific activity}}{\text{lysate volume} \times \text{reaction time}}$$

|  | Off-chip | On-chip |
|---|---|---|
| reaction velocity/$V_{max}$ ‡ | 0.78 | 0.48 |
| relative efficiency, also normalizing for reaction velocity | 1 | 21.6 |

\* For the off-chip assay only 1/30th of the reaction products were measured by liquid scintillation and the result reported is the readout multiplied by 30. For the on-chip assay only one half of the reaction products were captured by the streptavidin columns, and the result reported is the beta camera readout multiplied by 2. Results reported are the average of 3 representative experiments.
† The on-chip reaction uses a 33-fold higher hot to cold ATP ratio than the off-chip reaction.
‡ Calculated using the Michaelis-Menten equation Velocity = (Vmax × [substrate])/(Km + [substrate]), the Km for BCR-ABL p210 and Abltide of 27.6 µM and a peptide substrate concentration of 100 µM for the off-chip reaction and 25 µM for the on-chip reaction.

What is claimed is:

1. An apparatus for performing a microfluidic radioactivity based assay, comprising:
   a microfluidic chip with a microchannel system and at least one reaction element adapted to capture radioactively labeled molecules, the reaction element comprising:
      a plurality of reaction columns retaining surface functionalized beads fluidly connected to the microchannel system of the microchip; and
      a circulation chamber fluidic circuit fluidly connected to an entry port and to an exit port of each reaction column; and
   a solid state radiation detector coupled to the microfluidic chip;
   wherein radiation emitted from said microfluidic chip is detected; and
   wherein said functionalized beads can be removed from the reaction column to the circulation chamber through the exit port, mixed and returned to the reaction column through the column entry port.

2. An apparatus as recited in claim 1, wherein said surface functionalized beads retained in the plurality of reaction columns comprise affinity beads.

3. An apparatus as recited in claim 1, wherein said surface functionalized beads are functionalized with a coating of a plurality of enzyme specific antibodies, and wherein enzymes disposed in a liquid flowing through the reaction column bind to the antibodies on the surface of the beads.

4. An apparatus as recited in claim 3, wherein said surface functionalized beads comprise Protein G polystyrene beads functionalized with a coating of kinase specific antibodies.

5. An apparatus as recited in claim 1, wherein said microchannel system further comprises:
   at least one second reaction element within a flow path of the first reaction element.

6. An apparatus as recited in claim 5, wherein said second reaction element comprises:
   at least one second reaction column retaining affinity beads fluidly connected to the first reaction column; and
   wherein reaction substrates released from the first reaction column are captured by the second reaction column.

7. An apparatus as recited in claim 5, wherein said second reaction element comprises:
   at least one second reaction column retaining surface functionalized beads fluidly connected to the first reaction column;
   wherein reaction substrates released from the first reaction column are captured by the second reaction column.

8. An apparatus as recited in claim 1, wherein said radiation detector comprises:
   a position sensitive avalanche photodiode (PSAPD)-based solid state beta camera;
   wherein beta radiation emissions from the microfluidic chip are detected and quantified by the camera.

9. An apparatus as recited in claim 8, wherein said radiation detector further comprises:
   an aluminated Mylar film on a top surface of said radiation detector; and
   a Mylar sheet coupled to said aluminated Mylar film and said microfluidic chip disposed on a top surface of said Mylar sheet;
   wherein the radiation detector is shielded from visible light by the aluminated Mylar film and Mylar sheet.

10. An apparatus for performing a microfluidic radioactivity based assay, comprising:
    a microfluidic chip comprising:
       a microchannel system;
       a plurality of reaction columns configured to retain surface functionalized beads and adapted to capture radioactively labeled molecules and fluidly connected to the microchannel system;
       at least one mixing chamber fluidly connected to each of said reaction columns with at least two ports, said mixing chamber configured to receive, mix and recycle said surface functionalized beads to said reaction columns;
       a fluidic control system configured to control a fluid flow and a flow of surface functionalized beads through the microchannel system, mixing chambers and reaction columns; and
    a solid state radiation detector coupled to the microfluidic chip;
    wherein radiation emitted from said microfluidic chip is detected.

11. An apparatus as recited in claim 10, wherein said radiation detector comprises:
    a position sensitive avalanche photodiode (PSAPD)-based solid state beta camera;
    wherein beta radiation emissions from the microfluidic chip are detected and quantified by the camera.

12. An apparatus as recited in claim 11, wherein said radiation detector further comprises:
    an aluminated Mylar film on a top surface of said radiation detector; and
    a Mylar sheet coupled to said aluminated Mylar film and said microfluidic chip disposed on a top surface of said Mylar sheet;
    wherein the radiation detector is shielded from visible light by the aluminated Mylar film and Mylar sheet.

13. An apparatus as recited in claim 10, wherein said surface functionalized beads are functionalized with a coating of a plurality of enzyme specific antibodies, wherein enzymes disposed in a liquid flow through the reaction column bind to the antibodies on the surface of the beads.

14. An apparatus as recited in claim 10, wherein said surface functionalized beads comprise Protein G polystyrene beads functionalized with a coating of a plurality of a kinase specific antibody.

15. An apparatus as recited in claim 10, wherein said reaction columns comprise:
    a first reaction column fluidly connected to a second reaction column, wherein an output from the first reaction column flows through the second reaction column.

16. An apparatus for performing a microfluidic kinase radioactivity based assay, comprising:
a microfluidic chip comprising:
a microchannel system;
a plurality of first reaction columns fluidly connected to the microchannel system configured to retain surface functionalized beads coated with a kinase specific antibody and adapted to allow kinase reactions with at least one radioactive substrate;
a circulation chamber fluidic circuit fluidly connected to an entry port and to an exit port of each first reaction column, wherein a fluid comprising said surface functionalized beads flowing from the exit port of the first reaction column is circulated through the circulation chamber and back into a reaction element through the entry port of the first reaction column;
a second reaction column adapted to capture radioactively labeled molecules, said second column fluidly connected to at least one first reaction column;
a fluidic control system configured to control fluid flow through the microchannel system, circulation chamber and first and second reaction columns; and
a solid state radiation detector coupled to the microfluidic chip;
wherein kinases from a sample cell lysate bind to the kinase specific antibodies of the functionalized beads of the reaction columns and are captured;
wherein the captured kinases react with at least one radioactive substrate to produce a radioactive reaction product; and
wherein radiation emitted from said microfluidic chip is detected.

17. An apparatus as recited in claim 16, wherein said second reaction column is configured to retain solid state anion exchange beads.

18. An apparatus as recited in claim 16, wherein said kinase is a protein kinase.

19. An apparatus as recited in claim 16, wherein cycles of bead trapping, release and resuspension permit bead washing and solution exchanges to be performed within the first reaction column.

20. An apparatus as recited in claim 16, further comprising:
a computer and programming operably coupled to the fluidic control system and the radiation detector;
wherein the control of timing and sequence of fluid flow through the microfluidic chip are controlled by computer programming; and
wherein radiation detection is controlled and recorded.

* * * * *